United States Patent [19]

Kovacs

[11] Patent Number: 5,178,161
[45] Date of Patent: Jan. 12, 1993

[54] MICROELECTRONIC INTERFACE

[75] Inventor: Gregory T. A. Kovacs, Palo Alto, Calif.

[73] Assignee: The Board of Trustees of the Leland Stanford Junior University, Stanford, Calif.

[21] Appl. No.: 671,640

[22] Filed: Mar. 19, 1991

Related U.S. Application Data

[63] Continuation of Ser. No. 240,172, Sep. 2, 1988, abandoned.

[51] Int. Cl.$^5$ .............................................. A61N 1/05
[52] U.S. Cl. .................................. 128/784; 128/642; 128/419 R
[58] Field of Search ................... 128/639, 642, 419 R, 128/784, 734; 604/20

[56] References Cited

U.S. PATENT DOCUMENTS

| | | | |
|---|---|---|---|
| 4,539,995 | 9/1985 | Segawa | 128/639 |
| 4,573,421 | 3/1986 | Bulbara | 128/784 |
| 4,590,946 | 5/1986 | Loeb | 128/784 |
| 4,623,355 | 11/1986 | Sawruk | 128/642 |
| 4,628,933 | 12/1986 | Michelson | 128/784 |
| 4,632,116 | 12/1986 | Rosen et al. | |
| 4,785,812 | 11/1988 | Pihl et al. | 128/734 |
| 4,820,263 | 4/1989 | Spevak et al. | 604/20 |
| 4,837,049 | 6/1989 | Byers et al. | 128/784 |

OTHER PUBLICATIONS

"Two Research Efforts Spark Hope in Repair of Damaged Nerves", Michael Bowker, Los Angeles Times, May 28, 1988.
"Sci-fi microchip: the future of nerve repair", Eric Ly, The Stanford Daily, Apr. 21, 1988.
"Discovery may repair nerves", Kevin Montague, The Stanford Daily, Jul. 29, 1988.
"Development of Chronic Implant Neural Prosthesis Microelectrode Arrays", Kovacs et al., *IEEE Montech '87*, Nov. 10-12, 1987, pp. 152-155.
"Putting Brainpower in a Box", Christine Gorman, Time, Aug. 8, 1988, p. 59.
"Design and Implementation of Two-Dimensional Neural Interfaces", Kovacs et al., Stanford University Depts of Electrical Engineering.
"Stanford University General Purpose Microelectrode Fabrication Process", Kovacs et al., Stanford University Depts. of Electrical Engineering.
"Advances Toward Development of Microelectronic Axonal Interface Neuroprostheses", Kovacs et al., Stanford University Depts. of Electrical Eng'g.
"Implantable Monolithic Wafer Recording Electrodes for Neurophysiology", Llinas et al., Brain Unit Activity During Behavior, 1973, pp. 105-111.
"Bullfrog nerve regenration into porous implants", Anne F. Marks, American Association of Anatomists, *Anatomical Record* 163, 1969, p. 226.
"Regeneration Electrode Units: Implants for Recording . . . Freely Moving Animals", Mannard et al., *Science*, vol. 183, Feb. 8, 1974, pp. 547-549.
"Analysis and microelectronic design . . . from captured nerve fibres", Loeb et al., *Med. & Bio. Eng. & Comput.*, Mar. 15, 1977, pp. 195-201.

*Primary Examiner*—Kyle L. Howell
*Assistant Examiner*—Kennedy J. Schaetzle
*Attorney, Agent, or Firm*—Majestic, Parsons, Siebert & Hsue

[57] ABSTRACT

A microelectrode interface is disclosed for localizing the stimulation and recording of action potentials at a portion of a nervous system. The shapes of the electrodes are such that the number of ion flux lines actually intersecting a portion of the nervous system to be stimulated is increased or even maximized. This is accomplished by choosing microelectrodes of the shape such that they are at least as large in dimension at locations away from the other microelectrode as are locations close to the other microelectrode. The microelectrodes are on one side of a chip so that it is possible to stimulate a portion of the central nervous system by placing the microelectrodes alongside the portion. By employing microelectrodes on both sides of a chip or plate, the nervous system can be stimulated in a bipolar mode as well as the unipolar mode. The microelectrode on the back side also reduces noise. A circuit is disclosed for applying current only to one or more selected pairs of microelectrodes in an array of microelectrodes. Row and column select lines, switches and multiplexers are used for passing current only between pairs of microelectrodes at selected locations in the array for stimulating a portion of a nervous system only at selected locations.

24 Claims, 10 Drawing Sheets

MICROELECTRONIC INTERFACE

This is a continuation of application Ser. No. 240,172, filed Sep. 2, 1988 now abandoned.

BACKGROUND OF THE INVENTION

This application relates in general to a microelectronic interface which is particularly suitable for use in or with nervous systems.

Medical researchers have used electrical current to stimulate action potentials in axons or record such action potentials for many years. Typically, a microelectrode in the form of a needle is inserted into the axon in an animal, for example, and a second electrode is electrically connected to the animal at a distant point from the axon to be stimulated. Such techniques are disadvantageous since the electrical current must pass through a lengthy path through the animal's body. Therefore, the stimulating effect of the current is not localized to the axon so that the current is spread over a large portion of the body. For this reason a large current may be required to generate sufficient current density to have the desired stimulating effect in a particular axon. Such designs are thus wasteful of electrical current. If a large current is used, the useful life of the electrodes is reduced.

In U.S. Pat. No. 4,632,116, Rosen et al. describe a chip perforated with an array of holes for accommodating axons. Each hole contains one or more electrical contacts. The chip is inserted between the severed fascicle ends of the severed nerve so that the proximal axons will propagate through the holes prior to regenerating through paths formed by the degenerated distal axons. Through impulse monitoring, applying blocking potentials and placing selected pairs of proximal and distal contacts in electrical connection, it is stated that nerve impulses from axons in the proximal ends are routed to distal axons in order to restore normal impulse communication and nerve function.

While the chip device described by Rosen et al. in U.S. Pat. No. 4,632,116 marks a significant advance in neuroscience, the performance of the device is nevertheless not entirely satisfactory in many respects. Thus, in U.S. Pat. No. 4,632,116, the electrical contacts employed at the holes are circular or semicircular arcs at the inner surfaces of the holes. The circular or semi-circular arc shaped contacts serve as microelectrodes from which ion flux lines emanate for inducing action potentials in axons. However, when a circular microelectrode is used, the ion flux lines would tend to be diverted from the axon towards other parts of the body where stimulation is not intended. Where a semi-circular shaped pair of microelectrodes are used, the electrical resistance across the insulating gap separating the pair is typically much smaller than the electrical resistance across the axon separating the pair. For this reason, most of the ion flux lines would tend to concentrate in the gaps between the microelectrode and are not effective in inducing action potentials at the axon. Therefore such microelectrodes are not efficient in inducing action potentials in nervous systems. Furthermore, it may be difficult to fabricate tiny neural interfaces where the conducting electrical contacts are at the inner surfaces of the holes in the interface.

In the chip device described by Rosen et al., nerve impulses from axons in the proximal ends are routed to distal axons in order to restore normal impulse communication in nerve function. Thus, Rosen et al. contemplate a one-to-one mapping of nerve impulses so that the nerve impulses from axons in the proximal ends are routed to the distal axons to which they were originally connected before severance in order to restore normal impulse communication and nerve function. Thus Rosen et al. contemplate a one-to-one mapping in the routing of nerve impulses. Since some axons simply will not regenerate, it may not be even possible to route the impulses on a one-to-one basis. Also, it has not been shown that one-to-one mapping is necessary to revive the motor or sensory function of the body. Furthermore, since a nerve fiber can easily contain several thousand axons, the rerouting of the nerve impulses on a one-to-one mapping basis will require an enormous amount of work. It is therefore desirable to provide a more efficient device and method for restoring normal nerve function or for providing a human/machine interface.

It is therefore desirable to provide an microelectronic interface with improved characteristics.

SUMMARY OF THE INVENTION

Before the advent of the new chip introduced by Rosen et al. in U.S. Pat. No. 4,632,116, medical researchers lacked the proper tools which makes it possible to localize the effects of stimulation through electrical current or for detecting the local action potentials of axons. One aspect of the invention is based on the observation that the effects of stimulation or detection can be localized and improved by using a pair of microelectrodes on a chip or other carrier plate to stimulate or detect the action potential at a portion of the central nervous system.

Thus, one aspect of the invention is directed towards a method for causing or detecting an action potential in the portion of a nervous system by means of a device which comprises (a) a pair of microelectrodes supported on the same side of a plate in a medium which contains ions, and (b) means for applying or detecting an electrical potential difference between the pair when the portion of the nervous system is close to the pair but not between the pair. The method comprises placing the pair of microelectrodes adjacent to each other and adjacent to and alongside the portion of the nervous system. The method further comprises applying an electrical potential across the microelectrodes so that the ion flux lines caused by the potential across the microelectrodes pass from one microelectrode in curved paths intersecting the portion and then to the other microelectrode, so that the potential difference induced in the nervous system is localized to said portion.

Another aspect of the invention is directed towards the shape of microelectrodes. Since it is desirable to localize the stimulating effects of electrical current passing between a pair of microelectrodes and to maximize the stimulating effect of the current, it is therefore desirable to employ microelectrodes of a shape such that the number of ion flux lines passing between the pair actually intersect a portion of the nervous system to be stimulated is increased or even maximized; this will be referred to below as "focusing". This is accomplished by choosing microelectrodes shaped so that the ion flux lines passing through locations between the pair are increased.

Thus, another aspect of the invention is directed towards a device for causing or detecting change in the electrical potential in the portion of the nervous system where the device comprises a pair of microelectrodes in a medium which contain ions. The device further comprises means for applying or detecting an electrical potential difference between the pair. A part of each of said pair of microelectrodes is effective for causing or detecting action potentials in the portion of the nervous system through the movement of ions in the medium. When the applying means applies an electrical potential difference between the pair when the pair is close to the portion of the nervous system, such potential difference causes ions to move along flux lines passing the effective parts of the pair in the medium to induce an action potential in the portion. The effective part of each of said pair of microelectrodes is shaped so that said effective part is at least as large in dimension at locations away from the other microelectrode as at locations close to the other microelectrode to focus the ion flux lines at the portion when it is located between the pair, so that the action potential induced in the nervous system by the ions is localized.

While the device is particularly suitable for causing or detecting change in electrical potential in a portion of the nervous system, it is understood that the device can also be used for causing or detecting change in electrical potential in other mediums containing ions as well and all such applications are within the scope of the invention.

Yet another aspect of the invention is directed towards an improved chip configuration for stimulating or detecting action potentials. Thus, yet another aspect of the invention is directed towards a device for causing or detecting change in electrical potential in the portion of the nervous system. The device comprises a carrier plate in the medium which contains ions, a pair of microelectrodes on one side of said plate and means for applying or detecting an electrical potential difference between the pair in the same manner as those in other aspects of the invention described above. This device is particularly advantageous since the pair of microelectrodes are located on one side of the plate. Therefore conventional semiconductor processing techniques may be used for fabricating the device. A further improvement of the device includes another electrode on the back side of the plate; such electrode is effective in shielding the device from electrical noise, particularly when such electrode is grounded. According to another related but independent aspect of the invention, the carrier plate has a hole therein and electrical potentials may be applied across the microelectrodes on opposite sides of the plate as well as across the microelectrodes on the same side of the plate in order to stimulate a portion or the nervous system placed in the hole.

Still another aspect of the invention is directed towards a device for causing or detecting change in the electrical potential in the portion of a nervous system, where, at the same time, the impedance of the portion can also be measured. The impedance of the portion of a nervous system indicates the conditions of the electrodes as well as conditions of the tissue in the portion and yields valuable information on both the electrodes and the tissue. It is therefore desirable to be able to monitor the impedance of the portion while the portion is being stimulated. The device comprises a pair of microelectrodes in a medium which contains ions, a current source for passing current between the pair through the movement of ions along flux lines so that when the portion of the nervous system is close to the pair at least a portion of the current interacts with said portion to stimulate the nervous system. The device further comprises means for detecting electrical potential between the pair to record signals from said portion when said portion is close to said pair and means for connecting said current source in said detecting means to said pair so that when said current source passes a current through said current, said detecting means measures the impedance between the pair.

Another aspect of the invention is directed towards a device which includes an array of pairs of microelectrodes where current can be passed between a selected pair of microelectrodes to localize the effects of stimulation. The device is for causing or detecting change in electrical potential at selected locations in a portion of the nervous system. The device comprises an array of pairs of microelectrodes in the medium which contains ions, each pair placed at a desired location in or near said portion. The device also comprises means for passing a current between a pair of microelectrodes through the movements of ions along flux lines between the pair so that at least a portion of the current passes through a desired location in said portion to stimulate the nervous system; and means for enabling said current passing means to pass current between a selected pair of microelectrodes to stimulate said portion only at a desired location. Such a device is also useful for causing or detecting change in electrical potential at selected locations in a medium other than that of a nervous system; such applications are within the scope of the invention.

Still another aspect of the invention is directed towards a prosthetic device for replacing a portion of a person's body where the portion is used for performing mechanical movements. The device comprises a structure adapted for performing substantially at least one predetermined mechanical movement of the portion, a neural interface in the body connected to a nerve for controlling movements of the portion. The interface detects neural messages in the nerve. The device includes means within the body for transmitting the neural messages detected by the interface and means for storing at least one pattern of neural messages corresponding to the predetermined movement of the structure. The device also includes means for receiving the transmitted neural messages and means for comparing said one pattern with the neural messages received. The comparing means will provide an enabling signal when the received neural messages match said one pattern. The device includes means for controlling the movement of the structure. The controlling means responds to the enabling signal for causing the structure to perform substantially the predetermined movement.

DETAILED DESCRIPTION OF THE INVENTION

Figure 1:
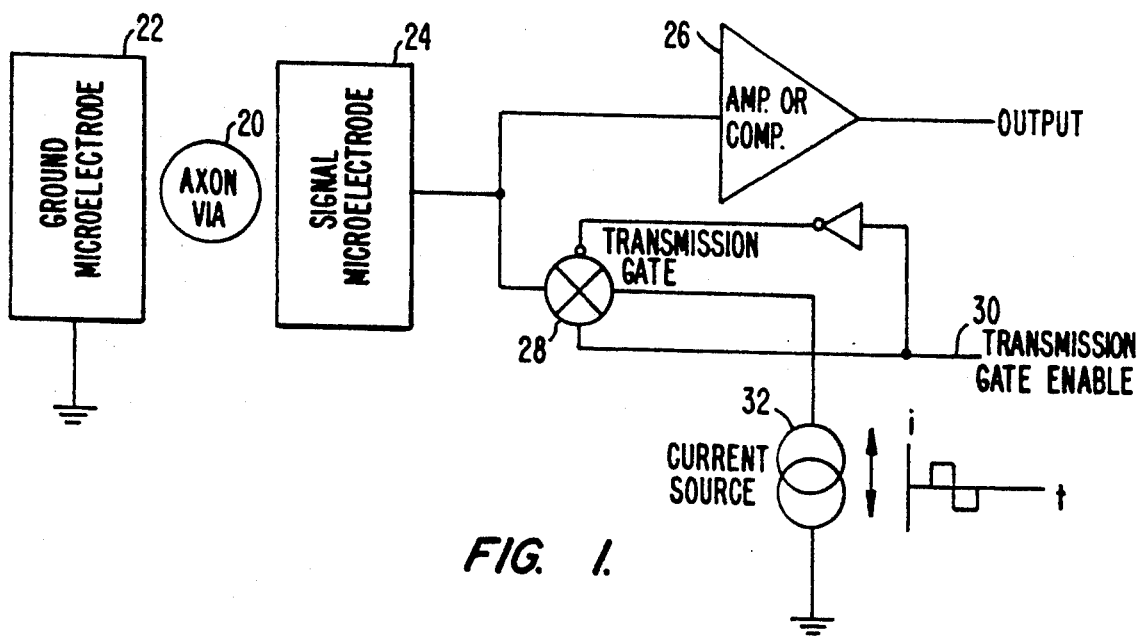
FIG. 1 is a block diagram of a microelectronic interface for stimulating or detecting an individual axon to illustrate the invention.

FIG. 1 is a block diagram of an electronic interface for stimulating or detecting the action potentials of an individual axon. As shown in FIG. 1, an axon 20 is sandwiched between a pair of microelectrodes 22, 24. Microelectrode 22 is grounded and microelectrode 24 is connected to an amplifier or comparator 26 and a transmission gate 26. The gate is enabled by signals on a transmission gate enable line 30. The gate controls the application of current from current source 32 to microelectrode 24. Thus, when the pair of microelectrodes are used for sensing action potentials at axon 20, enable line 30 causes gate 28 to disconnect current source 32 from microelectrode 34. The signal detected at microelectrode 24 is therefore amplified or compared to a threshold by amplifier (or comparator) 26 whose output indicates the action potential (or the presence on absence thereof) at axon 20. Where an analog output signal is desired, an amplifier 26 is used to amplify the signal from the microelectrode to provide the output. Where a digital signal is desired, comparator 26 is used to compare the signal from microelectrode 24 to a set threshold to indicate the presence or absence of action potential at axon 20.

Gate 28 is arguably not required if the current source can be set to 0. Since the entire electronic interface of FIG. 1 is intended to be implantable into the body of a human or other animals, the operational lifetime of the device is envisioned to be on the order of 25 years. Any longterm leakage currents would contribute to premature electrode failure. Since ideal current sources are not realizable, the inclusion of a transmission gate is therefore preferable.

Where the current applied to the pair of microelectrodes is used for stimulating axon 20, gate enable 30 applies a signal to gate 28 to permit current from current source 32 to be applied to microelectrode 24. Microelectrodes 22, 24 and axon 20 are immersed in extracellular fluids containing ions. The potential difference between the pair of microelectrodes will cause ions to flow between the two microelectrodes along ion flux lines (not shown). Some of the ions will interact with axon 20, thereby causing an action potential to be generated for the purpose of stimulation.

Figure 2A:
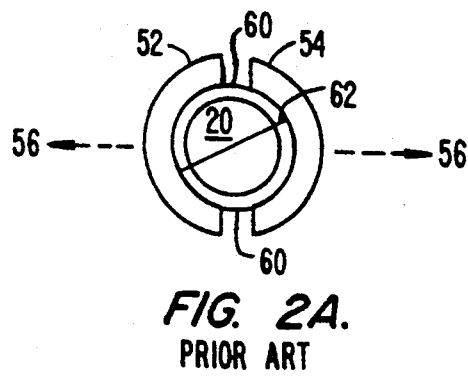
FIG. 2A illustrates the shape of a pair of microelectrodes used in the device disclosed by Rosen et al. referenced above.

As discussed above, it is desirable to localize stimulation or detection of action potential to a particular location in the nervous system. While the device disclosed by Rosen et al. has made it possible for such localization, the circular or semicircular arc-type microelectrodes at the inner surfaces of holes of the neural interface employed by Rosen et al. have many disadvantages as described above. As noted above, the semi-circular shaped microelectrodes are disadvantageous since the geometry causes the ion flux lines to be focused at the gaps between the microelectrodes instead of at the axon between the microelectrodes. This can be readily understood from FIG. 2A. From FIG. 2A, it will be observed that flux lines 60 between the microelectrodes 52, 54 are much shorter than flux line 62. Furthermore, axon 20 has a much higher electrical resistance compared to the extracellular fluid which fills the gaps between the microelectrodes. Therefore, ions moving along flux lines 60 will experience much lower electrical resistance compared to ions moving along flux line 62. For this reason, the ion flux lines will be concentrated and focused at the two gaps between the microelectrodes 52, 54 instead of at locations which would intersect axon 20.

In order to focus ion flux lines at the axon, it is desirable to choose a microelectrode shape which would increase the lengths of flux lines (such as flux lines 60 in FIG. 2A) between the microelectrodes not intersecting an axon located between the microelectrodes compared to the lengths of flux lines (such as flux line 62 in FIG. 2A) between the microelectrodes intersecting the axon. This invention is based on the observation that, to accomplish the above desired result, the dimensions of each microelectrode should be at least as large at locations away from the other microelectrode as at locations close to the other microelectrode. This will increase the concentration of flux lines at locations between the microelectrodes. A higher concentration of ion flux lines at or near the axon will increase the efficiency of stimulation.

Figure 2B:
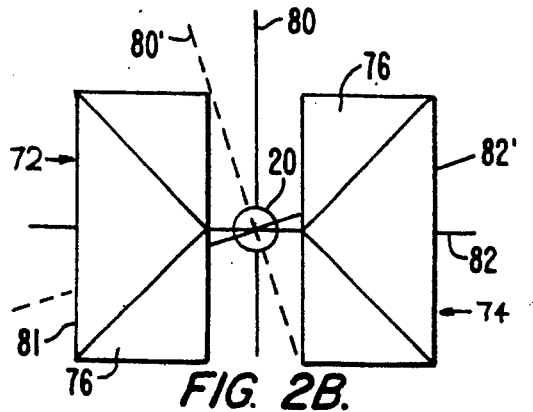
FIGS. 2B-2D illustrate the different geometries of a pair of microelectrodes to illustrate the different embodiments of the microelectrodes of this invention.
Figure 2D:
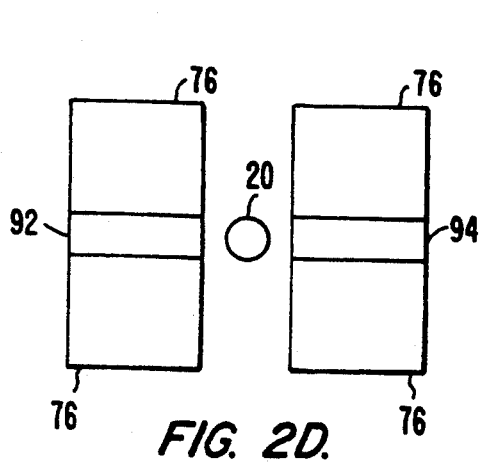
Figure 2C:
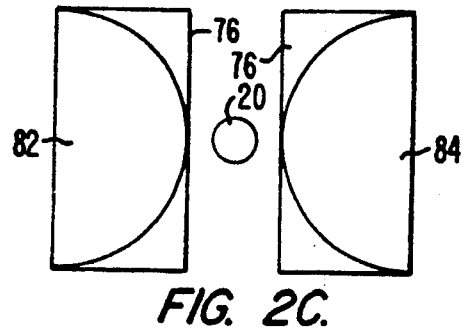

FIGS. 2B-2D illustrate three different split microelectrode shapes which can be advantageously used for focusing the ion flux lines at or in the vicinity of the axon. FIG. 2B illustrates a bow-tie shaped pair of microelectrodes comprise the exposed metal portions of a metal layer where the portions 72, 74 are not masked by an insulating layer 76. FIG. 2C illustrates a split-hemispherical or dual-parabolic geometry. FIG. 2D illustrates rectangular-shaped microelectrodes 92, 94. The desired geometry in FIGS. 2C, 2D is formed by covering portions of a metal layer by insulating layer 76 in the same manner as in FIG. 2B.

A direction (80) orthogonal to a line (82) passing through the axon 20 and the two electrodes may be defined as the orthogonal direction. It will be noted that, for all the microelectrodes in FIGS. 2B-2D, the dimension of each microelectrode in the orthogonal direction at locations away from the other microelectrode of the pair is at least as large as that at locations close to the other microelectrode. In the case of the microelectrodes in FIGS. 2B, 2C, their dimensions in the orthogonal direction at locations away from the other microelectrode are larger than those are locations close to the other microelectrode. In the case of FIG. 2D, their dimensions in the orthogonal direction remain unchanged irrespective of distance from the other microelectrode. It will also be noted that the above noted dimensional relations remain valid for most portions of each microelectrode (that is, not true only for a small portion of each microelectrode away from the other microelectrode, such as portion 81) even when lines, 82, 80 are moved to new positons 80', 82' so that the line 30' defines the orthogonal direction as shown in FIG. 2B.

Figure 3:
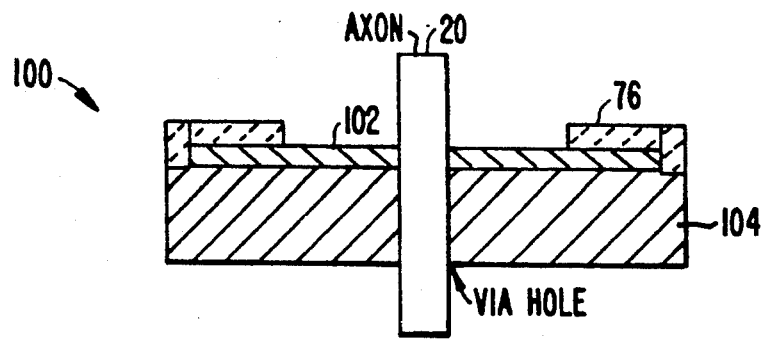
FIG. 3 is a cross-sectional view of a pair of microelectrodes, a supporting plate, an insulating layer and an axon to illustrate the preferred embodiment of the invention.

FIG. 3 is a cross-sectional view of a pair of microelectrodes to illustrate the preferred embodiment of the invention. As shown in FIG. 3, the microelectrodes can be conveniently formed by a metal layer 102 supported by a carrier plate 104 made of an insulating or semiconducting material. The shape of the electrode can be conveniently selected by covering portions of the metal layer by insulating layer 76 in order to form the microelectrodes 72, 74, 82, 84, 92, 94 as shown in FIGS. 2B-2D. The interface 100 shown in FIG. 3 is advantageous since the microelectrodes are formed on one side of plate 104 instead of at inner surfaces of holes as in Rosen et al. Since the microelectrodes are formed on a side of a carrier plate, conventional semiconductor processing techniques of masking and etching can be conveniently applied to fabricate the neural interfaces. Such conventional semiconductor processing techniques cannot readily be used for fabricating the device disclosed by Rosen et al.

Figure 4A:
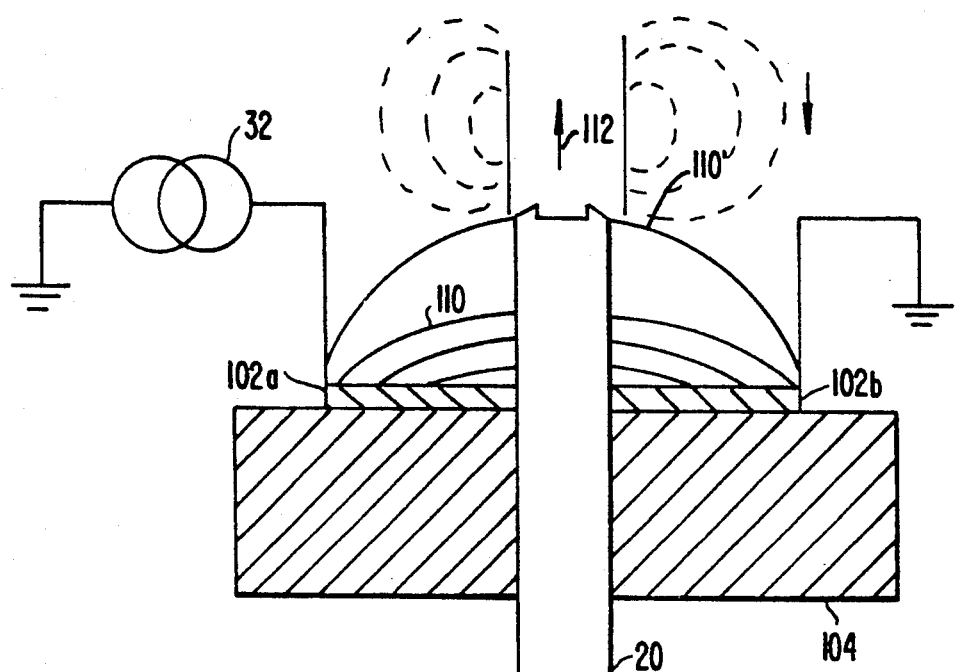
FIGS. 4A-4E are illustrations of ion flux patterns for different microelectrode operating modes to illustrate the operation of the invention.

FIGS. 4A-4E are partially schematic and partially cross-sectional views of a neural interface to illustrate the invention. Identical parts in the different figures in this application are identified by the same numerals. As shown in FIG. 4A, the interface includes metal layers 102a, 102b supported by a carrier plate 104. A current source 32 is connected to and applies a current to layer 102a and layer 102b is grounded. Current, therefore, flows between the metal layers 102a, 102b by the movement of ions along ion flux lines 110. The ions moving along such flux lines interact with axon 20 to induce an action potential therein. Since the travel of the action potential in the downward direction is blocked by the metal layers and the carrier plate 104, the action potential in axon 20 would travel primarily in the upward direction 112.

The same microelectrodes 102a, 102b may be used for sensing the action potentials traveling in axon 20. As is evident from FIGS. 1 and 4A, when an action potential is present in axon 20 in the vicinity of layers 102a, 102b, the action potential will cause ions to move as shown in dotted lines 120 as shown in FIG. 4A. Since layer 102b is grounded, it will remain at ground potential. In the detecting mode, layer 102a will be connected to an amplifier or comparator 26 instead of current source 32 as shown in FIG. 1. Thus, the potential induced in layer 102a by the ions relative to ground will be sensed and detected by amplifier or comparator 26 to indicate the presence of the action potential in axon 20.

The arrangement of FIG. 4A is advantageous over conventional stimulation devices where the two electrodes are far apart so that the stimulation is not localized. In the arrangement in FIG. 4A, since the two microelectrodes 102a, 102b are close together, the ion flux lines 110 will be concentrated in the area of the axon so that a significant part of the current flowing between the two microelectrodes will be effective in inducing an action potential in axon 20. Similarly, for detection purposes, since the two microelectrodes are placed close to each other, microelectrode 102b will provide an accurate reference voltage for measuring and detecting the action potential in axon 20. In conventional devices, however, the ground reference electrode is placed far apart from the other electrode so that the noise recorded will likely be increased.

Figure 4B:
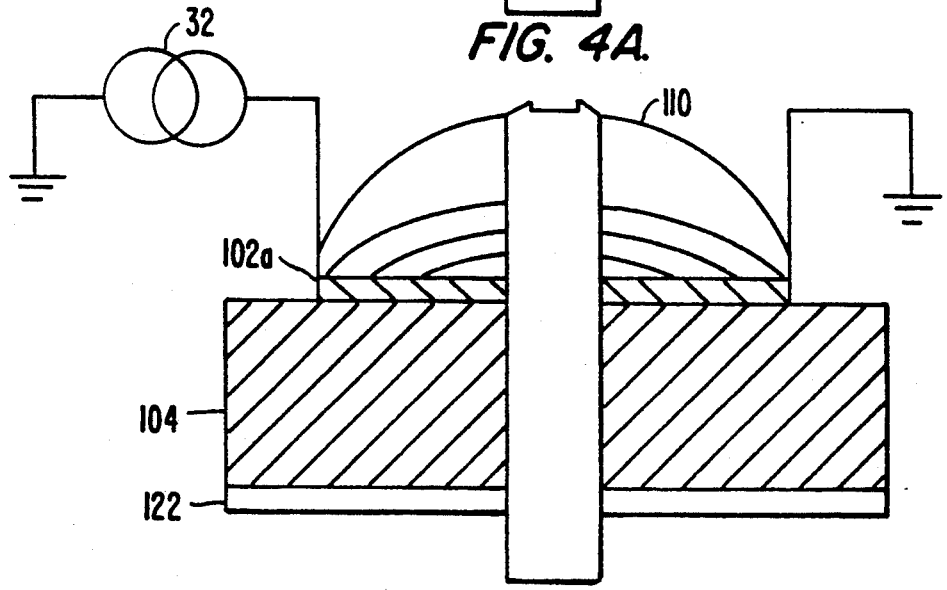

FIG. 4B illustrates an arrangement essentially the same as that in FIG. 4A except that the arrangement includes an additional electrode 122 on the backside of carrier plate 104. Since the movement of ions from microelectrode 102a to electrode 122 is prevented by plate 104 which is an insulator or a semiconductor, electrode 122 will have no effect on ion flux line patterns so that the ion flux lines 110 are unaffected by the additional electrode 122. The additional electrode 122 is useful for a number of purposes. Particularly where electrode 122 is also grounded, it provides a shield for electrode 102a from other electrical noise in its vicinity.

Figure 4C:
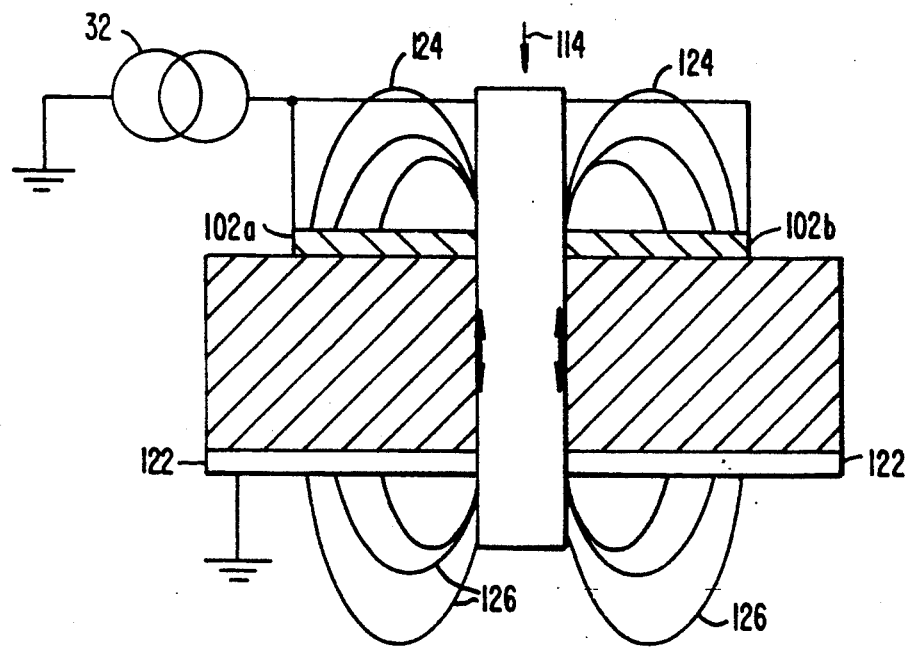

Alternatively, and as shown in FIG. 4C, electrode 122 may be used as a reference ground electrode so that current applied to both microelectrodes 102a, 102b causes a "bipolar" flux line pattern as shown in FIG. 4C. As shown in FIG. 4C, plate 104 has a hole for passage of an axon. Thus ions would travel from microelectrodes 102a, 102b along lines 124 towards axon 20 to induce an action potential. The charges thus transferred to axon 20 would travel along axon 20 downwards along the direction 114 and cause ions to flow along flux lines 126 towards electrode 122, thereby also inducing an action potential in axon 20. The arrangement in FIG. 4C may be advantageous since a bipolar arrangement may be more efficient than a unipolar arrangement.

Figure 4D:
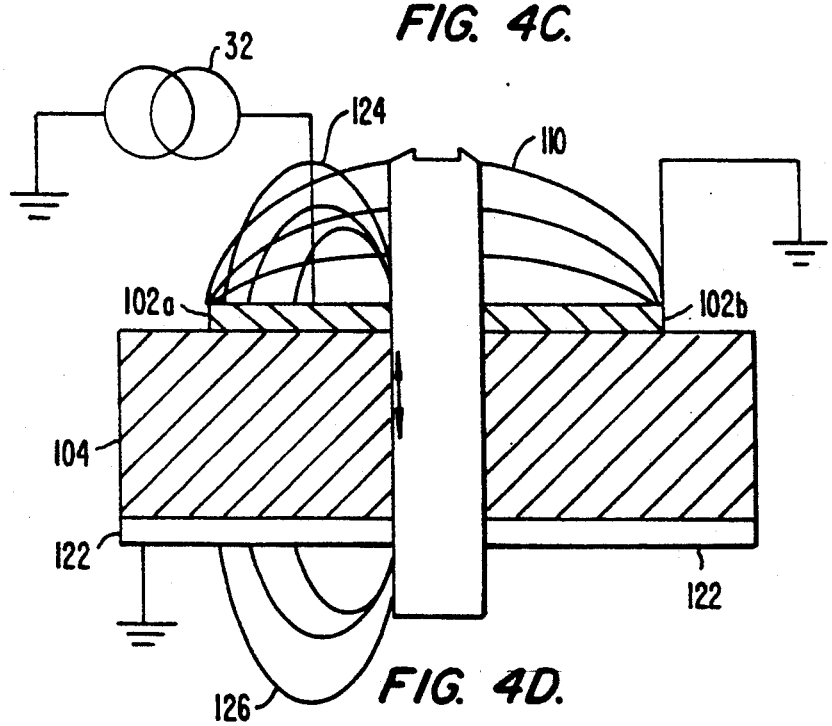

Yet a different arrangement employing the electrodes 102a, 102b and 122 is illustrate in FIG. 4D. As shown in FIG. 4D, the ion flux lines will be a combination of those in the unipolar operation of FIG. 4A and bipolar operation of FIG. 4C.

Figure 4E:
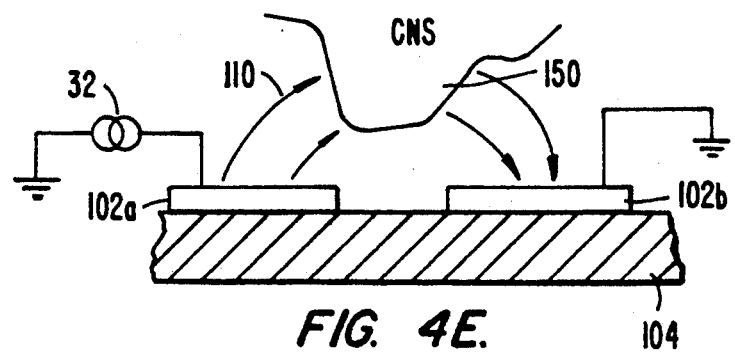

The arrangement of FIG. 4E illustrates the use of the device shown in FIGS. 3, 4A-4D for stimulating or detecting action potentials in a portion of a central nervous system. As shown in FIG. 4E, this can be done by placing the microelectrodes 102a, 102b adjacent each other and adjacent to but alongside a portion of a central nervous system 150. Ions will move along flux lines 110 to interact with portion 150 so as to induce neural firing(s) therein. Where microelectrode 102a is connected to an amplifier or comparator instead of a current source 32 in a manner illustrated in reference to FIG. 1, the same arrangement may be used for sensing neural firing(s) in portion 150. Thus in the arrangement of FIGS. 3, 4A-4E, by putting the two microelectrodes on one side of a carrier plate, it is possible to localize and concentrate the ion flux lines to focus on a portion of a nervous system not passing through any via holes between the microelectrodes, but onto a portion which is adjacent to the microelectrodes. In such manner, the arrangement may be adapted for stimulating or detecting action potentials of portions of the central nervous system instead of axons.

While in the above description the reference electrodes are described as being grounded, it will be understood that other reference voltages instead of ground voltage may be applied instead. Alternatively, the reference electrode can be left open circuit. Such variations are within the scope of the invention. In the above description, the current flow is carried sequentially by positively charged ions as well as negatively charged ions.

Figure 5:
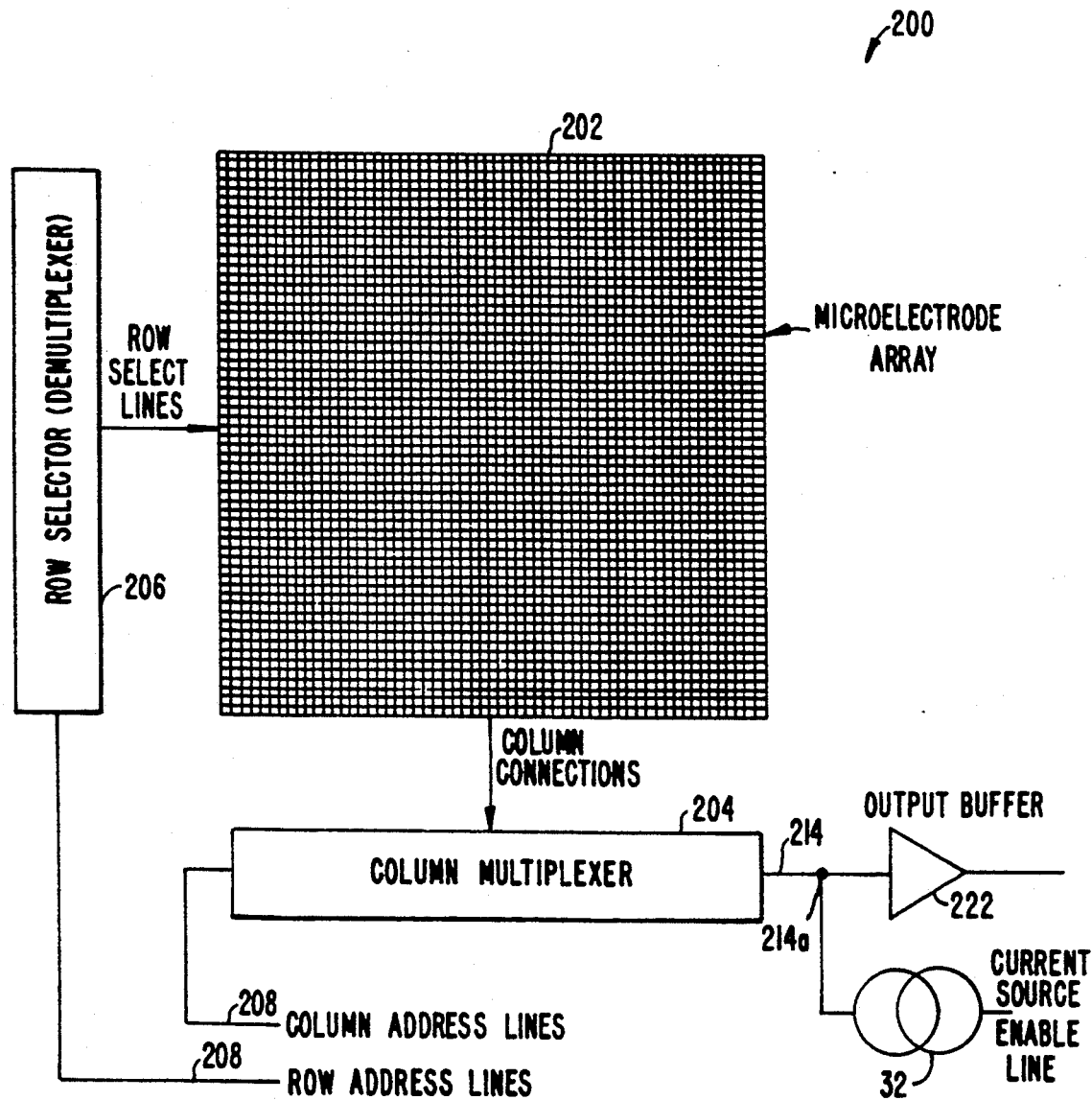
FIG. 5 is a block diagram of an array of microelectrodes and circuits for selectively stimulating and recording at a particular pair of microelectrodes in the array to illustrate a first alternative embodiment of the invention.

FIG. 5 is a block diagram of an array of microelectrodes and circuits for selectively stimulating and detecting at a particular pair of microelectrodes in the array to illustrate an alternative embodiment of the invention. As shown in FIG. 5, neural interface 200 includes a two-dimensional array 202 of pairs of microelectrodes arranged in a manner shown in more detail in FIG. 6.

Figure 6:
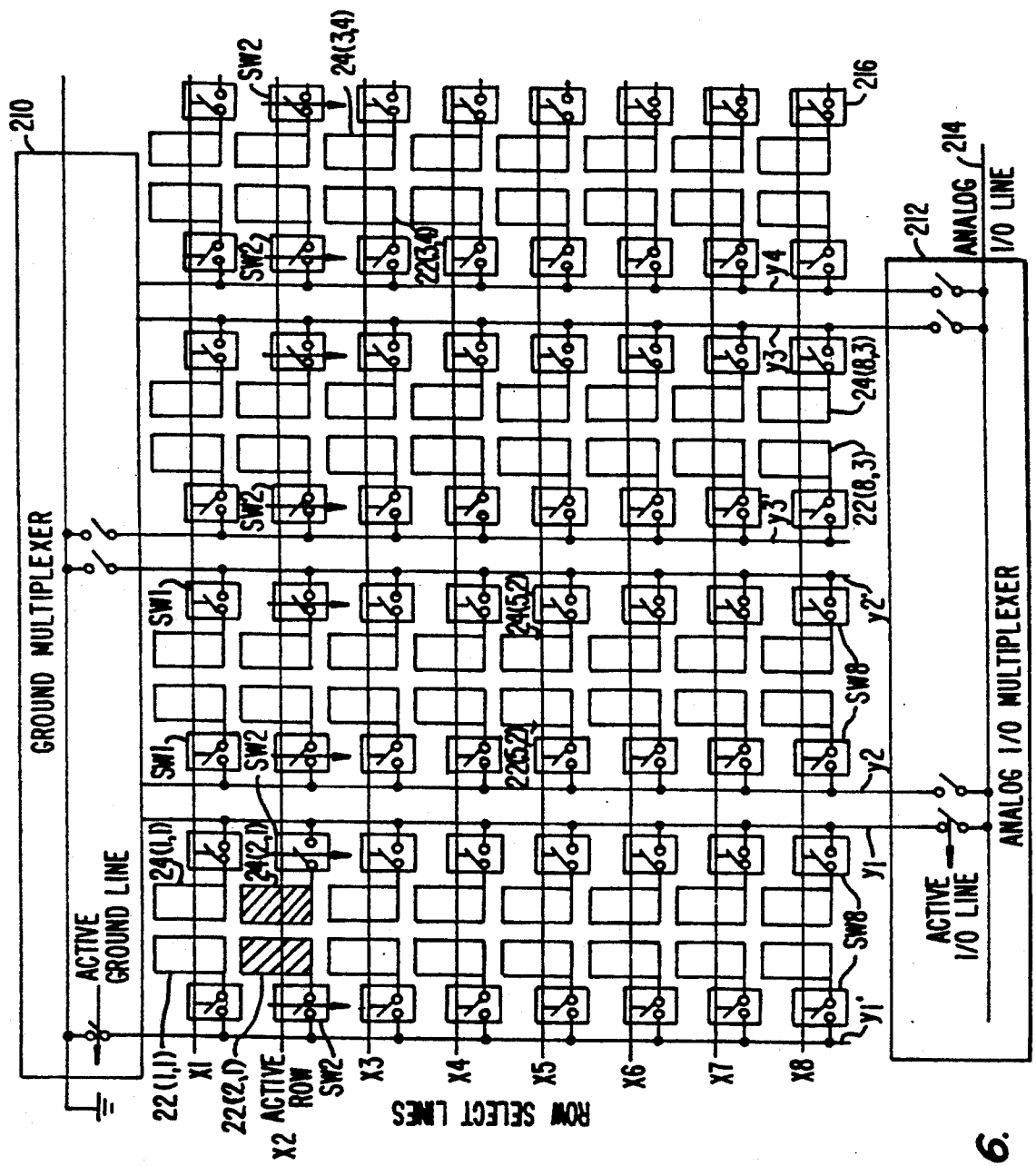
FIG. 6 shows in more detail a portion of the circuit of FIG. 5 and illustrates in more detail a portion of the microelectrode array and a column multiplexer of FIG. 5.

FIG. 6 shows in more detail a portion of the microelectrode array and the column multiplexer of FIG. 5. Only a portion of array 202 is shown in FIG. 6. As shown in FIG. 6, array 202 is a two-dimensional array of pairs of microelectrodes 22(x,y) and 24(x,y), where x and y indicate the coordinates of the pair in the array. Assuming the row of microelectrodes on top of FIG. 6 is the first row in the array and the column of microelectrodes in the extreme left being the first column of microelectrodes in the array, the extreme left pair of microelectrodes in the first row of the array has the coordinates (1,1) so that the pair of microelectrodes are identified by the numerals 22(1,1), 24(1,1). The remaining pair of microelectrodes may be identified in a similar manner such as 22(2,1), 24(2,1) and so on. The first row of pairs of microelectrodes are addressed by a row select line x1, the second row addressed by the row select line x2 and so on.

Since each pair of microelectrodes contains two microelectrodes, (which may be referred to below simply as the left microelectrode and right microelectrode) and since stimulation or detection is accomplished by having two microelectrodes in a pair at different electrical potentials, each pair of microelectrodes must be addressed by two different select lines. In the configuration of FIG. 6, each column of pairs of microelectrodes is addressed by two column select lines, it being understood that two row select lines may be used instead. Thus, the column of the left microelectrodes 22(x,1) is addressed by the column select line y1'; the column of the right microelectrodes 24(x,1) is addressed by the column select line y1. Similarly the column of the left microelectrodes 22(x,3) is addressed by the column select line y3' whereas the column of the right microelectrodes 24(x,3) is addressed by the column select line y3. The column select lines y1', y2', ... yn', where n is a positive integer, are connected to a ground multiplexer 210. The column select lines y1, y2, ... yn are connected to an analog I/O multiplexer 212. Ground multiplexer 210 operates to ground the particular column of the left or right microelectrodes. Multiplexer 212 enables the voltage on the analog I/O line 214 to be applied to another column of the left or right microelectrodes.

Thus, if the pair of microelectrodes 22(2,1), 24(2,1) is to be selected for either stimulation or recording of action potential, ground multiplexer 210 causes the column select line y1' to be connected to ground and multiplexer 212 causes the current in line 214 to be applied to column select line y1. A row selector (not shown in FIG. 6) applies a signal to the row select line x2. The row select lines are not connected directly to the microelectrodes but are used only to close switches. Thus, when a signal is applied to the row select line x2, the signal causes switches sw2 for the second row of microelectrodes to close. The closing of the switches causes the microelectrode 22(2,1) to be connected to ground through line y1' and the current from line 214 to be applied to microelectrode 24(2,1) through column select line y1. The pair of microelectrodes at the location (2,1) is therefore effective for stimulation purposes. The remaining pairs of microelectrodes in the first column are not activated since the switches for such pairs are not closed. For the remaining pairs of microelectrodes in the second row, even though their corresponding switches have been closed by the signal on the row selector line x2, no current or potential difference is applied across their corresponding column select lines by multiplexers 210, 212. For this reason the pair of microelectrodes at location (2,1) is the only one which is effective for stimulation purposes. In a similar manner, any pair of microelectrodes may be selected by means of the two multiplexers and the row and column select lines in a manner similar to that described above.

It will be noted that the above described manner of addressing the microelectrodes bears great similarity to the addressing of random access memories. Hence, the multiplexers 212, 210 and the row and column select line may be implemented in integrated circuit chips or printed circuit board level designs in a manner conventional in memory technology. While only eight rows and four columns of microelectrodes are shown in FIG. 6, it will be understood that array 202 may include many more or fewer pairs of microelectrodes as needed. For example, the array may contain pairs of microelectrodes of a number which matches approximately the number of axons in a neuron fiber, with each pair of microelectrodes destined for stimulating or recording action potentials in one axon.

Returning now to FIG. 5, column multiplexer 204 includes both the ground and analog I/O multiplexers 210, 212 of FIG. 6. Row selector 206 is used for applying signals to the row select lines in a manner described above. Signals instructing multiplexer 204 and selector 206 as to which pair of microelectrodes is to be selected are carried on column and row address lines 208.

Device 200 may be used for stimulation and/or recording purposes. Array 202 is placed in contact or in the vicinity of a portion of a nervous system to be stimulated or recorded from. Current from source 32 is then applied through line 214 to a particular selected pair of microelectrodes for stimulating the portion of the nervous system at a particular location where the effect of such stimulation is localized. Where recording of action potential is desired, line 214 is connected through a gate to amplifier or comparator 26 in order to detect the action potential detected by a particular pair of microelectrodes so as to detect the action potential at a selected location of the portion. The circuit of FIG. 5 differs from that of FIG. 1 in that an output buffer 222 is connected to a common node 214a with source 32 (enabled or disabled through a current source enable line) which is connected to multiplexer 204 through line 214.

The circuit design of FIG. 5 is advantageous in that, when source 32 is used to apply a current to a pair of microelectrodes, the output of buffer 222 is the voltage across the microelectrodes which is proportional to the current which is flowing between the pair of microelectrodes selected. The magnitude of the current, flowing between the pair of microelectrodes indicates the impedance between the microelectrodes. Since the current flowing between the microelectrodes interacts with a portion of the nervous system, the magnitude of the current also indicates the impedance of the portion of the nervous system interacting with the current plus the impedance of the microelectrodes. The output of buffer 222 therefore indicates the impedance of the portion of the nervous system interacting with the current across the pair. The impedance of the portion of the nervous system indicates the condition of the tissue in such portion. The circuit of FIG. 5 therefore permits the condition of the portion of the nervous system stimulated to be detected while the portion is being stimulated; this yields valuable information on the nervous system.

Figure 7:
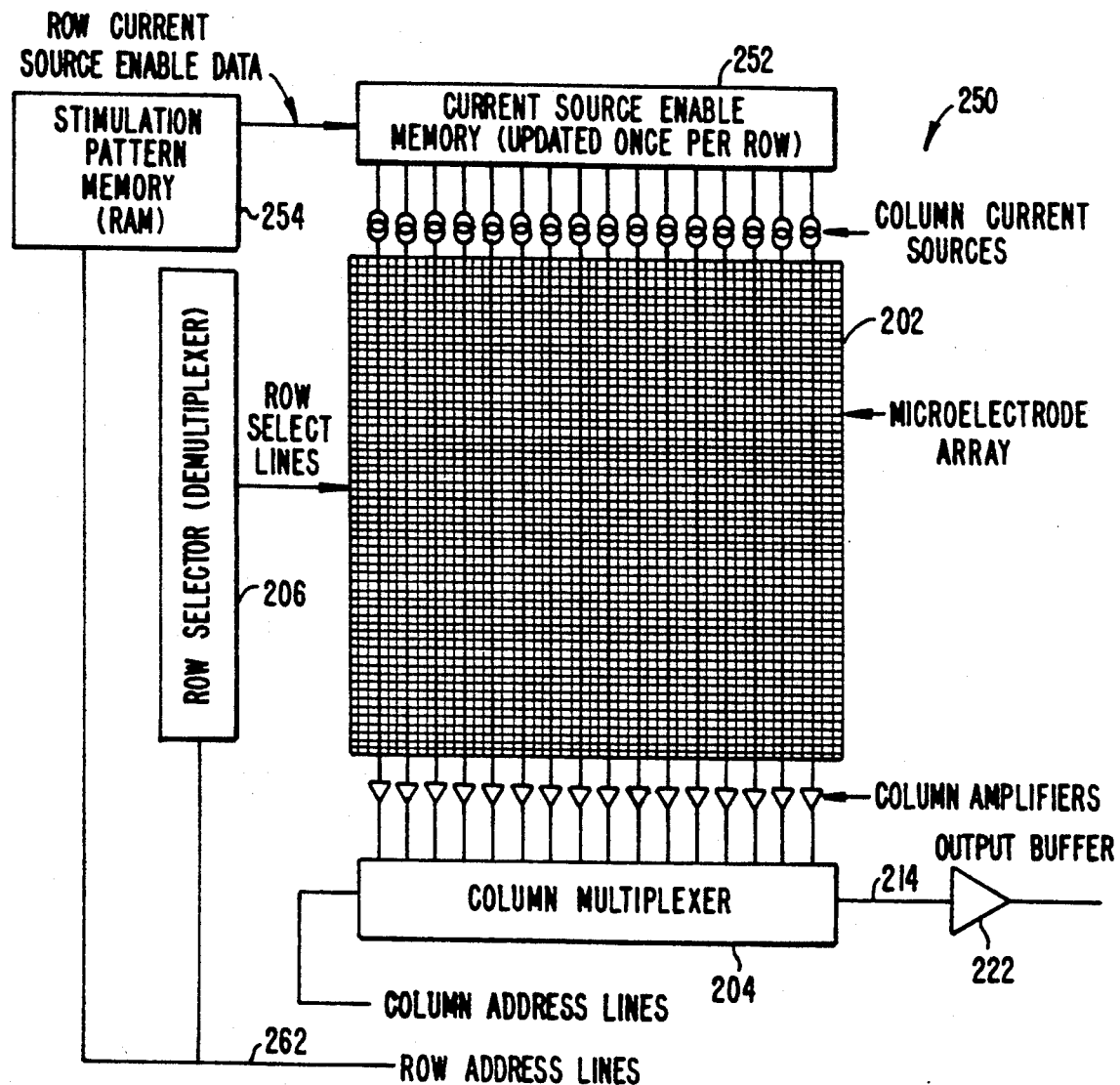
FIG. 7 is a block diagram of a microelectrode array and circuitry for stimulating at more than one pair of microelectrodes and recording at a microelectrode pair to illustrate the preferred embodiment of the invention.

FIG. 7 is a block diagram of a microelectrode array in circuits for stimulating at more than one pair of microelectrodes and recording at a microelectrode pair to illustrate the preferred embodiment of the invention. As shown in FIG. 7, the neural interface 250 has a configuration similar to that of interface 200 of FIG. 5; identical parts are indicated by the same numerals in the two figures. Neural interface 250 of FIG. 7 differs from interface 200 of FIG. 5 in that interface 250 permits stimulation at more than one location at any time. This is implemented by means of a memory 252 and a stimulation pattern memory 254. In the preferred embodiment illustrated in FIG. 7, the array 202 is activated one row at a time as in FIG. 5. Thus in order to stimulate at more than one location in the portion of a nervous system, current is passed through more than one pair of microelectrodes in a given row that is activated. For this reason it is preferable to employ a current source for each column of microelectrodes, as shown in FIG. 7. Memory 252 stores a 1 or a 0 for each column of pairs of microelectrodes. A value of 1 (or 0) stored in memory 252 for a column will cause the current source for such column to apply a current to the select line connected to the column of microelectrodes; a value of 0 (or 1) will not cause the current source to apply a current to the column select line for such column of microelectrodes. Since only one row of pairs of microelectrodes is activated at any one time, current will be passed only to the pairs of microelectrodes in such row selected in accordance with the pattern stored in memory 252. The pattern in memory 252 is updated once for each row by the data stored in memory 254 which may be a random access memory. Row selector 206 is activated by signals on a row address lines 262 to activate each row in the array. Signals on the row address lines also cause memory 254 to send row current source enable data to memory 252 to update it for each row.

Figure 8:
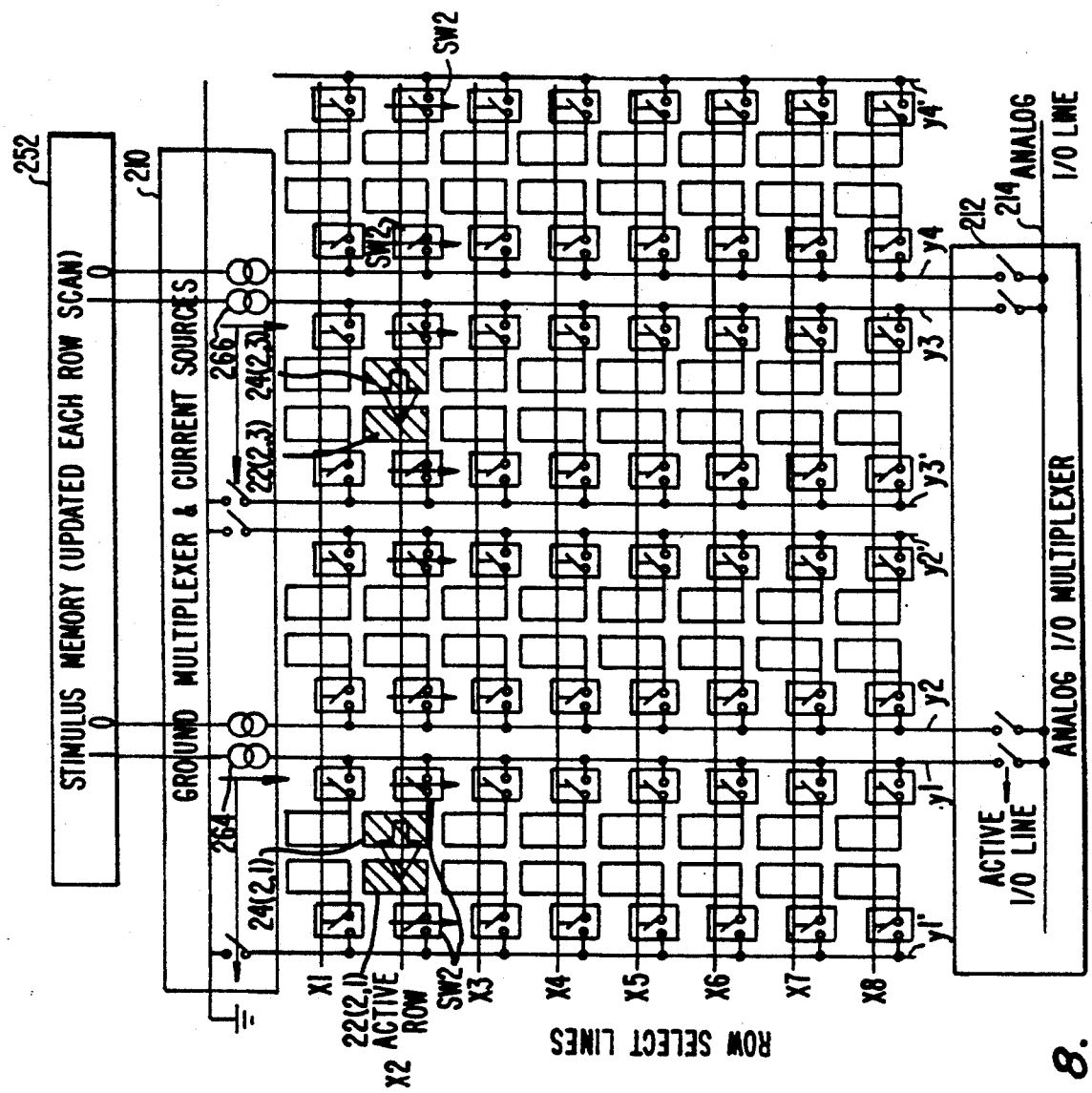
FIG. 8 shows in more detail a portion of the circuit of FIG. 5 and illustrates in more detail a portion of the microelectrode array and a column multiplexer of FIG. 7.

FIG. 8 shows in more detail a portion of the microelectrode array and of the column multiplexer of FIG. 7. As in FIGS. 5 and 6, column multiplexer 204 contains a ground multiplexer 210 and an analog I/O multiplexer 212. Ground multiplexer 210 causes one or more select lines, such as column select line y1', y3' to be grounded. Memory 252 will cause current to be applied by source 264 to column select line y1 and source 266 to apply a current to select line y3. If the row select line x2 is also activated to close the switches sw2 in such row, current will flow from source 264, switch sw2, microelectrode 24(2,1), microelectrode 22(2,1) switch sw2, and select line y1' to ground. Between the pair of microelectrodes 22(2,1), 24(2,1), current is carried by ions moving along ion flux lines between the microelectrodes where the ions interact with a portion of a nervous system to stimulate the portion at a particular location adjacent to the pair of microelectrodes. In the same manner, current flows from source 266 through switch sw2, microelectrode 24(2,3), 22(2,3), switch sw2 and column select line y3' to ground. The ions flowing between such pair of microelectrodes also stimulate the portion of the nervous system at a location different from that stimulated by the current flowing between the microelectrode pair 22(2,1), 24(2,1). In such manner, interface 250 is used to stimulate a portion of a nervous system at more than one location substantially simultaneously.

While multiplexer 212 is not necessary for stimulation purposes, it is needed when action potentials at particular locations at the portion of the nervous system are detected. Multiplexer 212 is operated in a manner similar to that of FIG. 6 in conjunction with multiplexer 210 to record the action potential at a particular (x,y) location in array 202 at any one time. Multiplexer 212 and line 214 may also be used in a manner described above in reference to FIG. 5 for detecting the impedance of a portion of a nervous system at a particular location while the portion is being stimulated at such location. The impedance sensed at such location will indicate the condition of the microelectrodes and of the tissues of the portion at such location which will be useful for diagnostic purposes.

Figure 9:
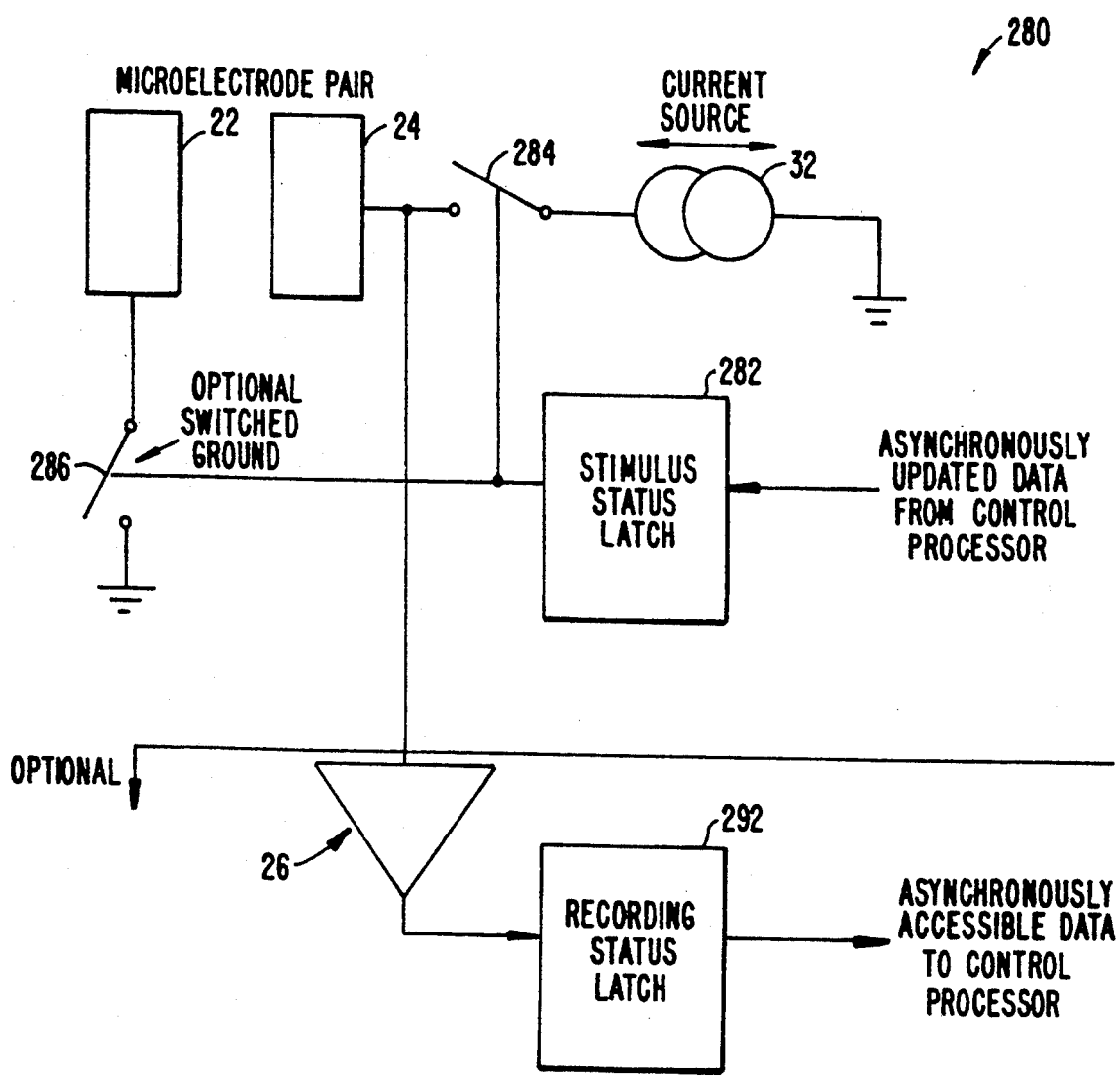
FIG. 9 illustrates an alternative embodiment of a circuit for stimulating and recording at a microelectrode pair to illustrate a second alternative embodiment of the invention.

FIG. 9 illustrates a circuit for stimulating and recording at a pair of microelectrodes to illustrate a second alternative embodiment of the invention. In FIGS. 5-8, the array of microelectrodes are selected or addressed by selecting a particular row and one or more columns at a time, and then selecting the next row and one or more columns. FIG. 9 illustrates another approach which allows any pair of microelectrodes to be selected for the purpose of stimulation and/or recording. As shown in FIG. 9, for stimulation purposes, each pair of microelectrodes 22, 24 is controlled by a stimulus latch (or flip flop) 282. Signals from a control processor (not shown) updates the value in the latch; if the value is of one value, for example 1 latch 282 will cause switch 284 to close. Current from source 32 will then pass between microelectrodes 22, 24 as before for stimulation purposes. In the preferred embodiment, latch 282 will also close switch 286 to ground microelectrode 22 to localize the current flow to the areas between the microelectrodes. The impedance between the microelectrodes can also be read by means of an amplifier via multiplexers as in previous embodiments. Comparator 26 detects the presence or absence of an action potential and this information is stored in latch 292 for read-out by a control processor (not shown).

The circuit is FIG. 9 resembles a static RAM in operation. The advantage of the circuit of FIG. 9 is that for both stimulation and recording purposes, the pairs of microelectrodes need not be selected or addressed on a row by row basis but can be in any arbitrarily selected pattern. This allows more flexibility in stimulation or recording at the cost of more circuitry on the chip. Furthermore, continuous stimulation and recording are possible since the value of the latch will remain unchanged until it is updated. The latch can also be updated asynchronuously to other operations in the array such as scanning for recording purposes.

Figure 10:
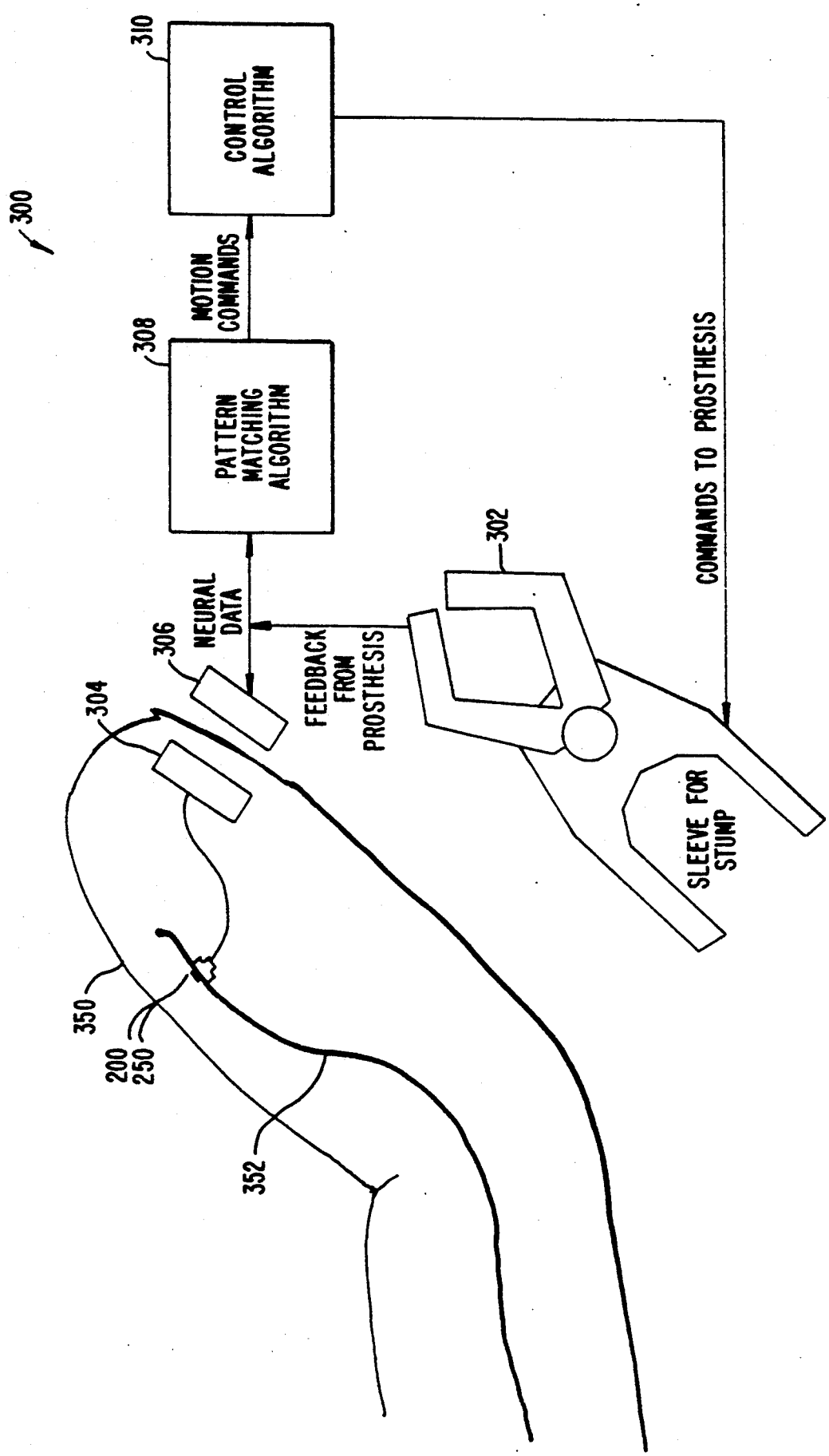
FIG. 10 is a block diagram of an interface system for motor prosthesis to illustrate the preferred embodiment of the invention.

FIG. 10 is a conceptual diagram of a prosthetic device which operates in response to neural messages from the brain of a person. As shown in FIG. 10, prosthetic device 300 includes a structure 302 which replaces a portion of a person's body, such as a hand which may have been accidentally severed. Structure 302 is adapted to perform certain of the predetermined functions normally performed by the hand. Device 300 responds to neural messages transmitted by a transceiver 304 which may be implanted in the stump of the limb. Transceiver 304 receives neural messages from a neural interface which may simply be device 200 or 250 of FIGS. 5 and 7. As described above in reference to FIGS. 5 and 7, action potentials at different locations are detected by pairs of microelectrodes in the array 202 which are then supplied to amplifier or comparator 26. Transceiver 304 transmits the actual output of the comparator or amplifier 26 together with the location information of the pair of microelectrodes actually providing the output.

Such transmitted information is received by a transceiver 306 in device 300. Such information received by transceiver 306 over a time period adequate to account for all pairs of microelectrodes in the array then form a pattern of neural messages representative of the neural messages detected by the neural interface. The limb stump 350 contains a nerve 352 for controlling the mechanical movement of the limb and carrying sensory information from the limb, where the nerve has been severed. The neural interface 200 or 250 is connected to nerve 352 in such manner that the interface is inserted between the surgically severed ends of nerve 352, so that the action potentials detected by the interface accurately represent the neural messages carried by the nerve. Thus the neural information received by transceiver 306 sampled over a time period adequate to cover all pairs of microelectrodes in the array in the interface, such information is compared to patterns of neural messages stored in pattern matching block 308. The patterns of neural messages stored in block 308 each correspond to a particular desired movement of the hand. When the information received by transceiver 306 matches a particular pattern stored, pattern matching block 308 will provide a motion command to control 310. Control 310 responds to a motion command for controlling the movement of structure 302 in order to perform a movement substantially the same as the desired limb movement corresponding to the pattern identified in pattern matching block 308.

Thus pattern matching block 308 stores a number of patterns, each pattern corresponding to a desired limb movement in a particular motion command. Control block 310 contains algorithms and circuits for controlling the movement of structure 302 so that structure 302 will perform substantially the desired hand movement in response to the corresponding motion command from pattern matching block 308. In such manner movement of structure 308 can be controlled by neural impulses from nerve 352 in a manner so that the movement of structure 302 will approximate the movement of the limb which is replaced by the structure in accordance with the person's desire as represented by the nerve impulses in nerve 352. Pattern matching block 308 and control block 310 may be implemented in a combination of hardware and software. Control block 310 contains algorithms which cause the structure 302 to perform a particular movement called for by the corresponding command from block block 308. Such algorithms are disclosed, for example, in *Robots and Telechirs*, by M. W. Thring, Ellis Horwood Limited, Chichester, 1983, ch. 3, 4, 5, 6, and in *Control Dynamics of Robotic Manipulators*, by J. M. Skowronski, Academic Press, Inc., Orlando, Fla., 1986.

Figure 11:
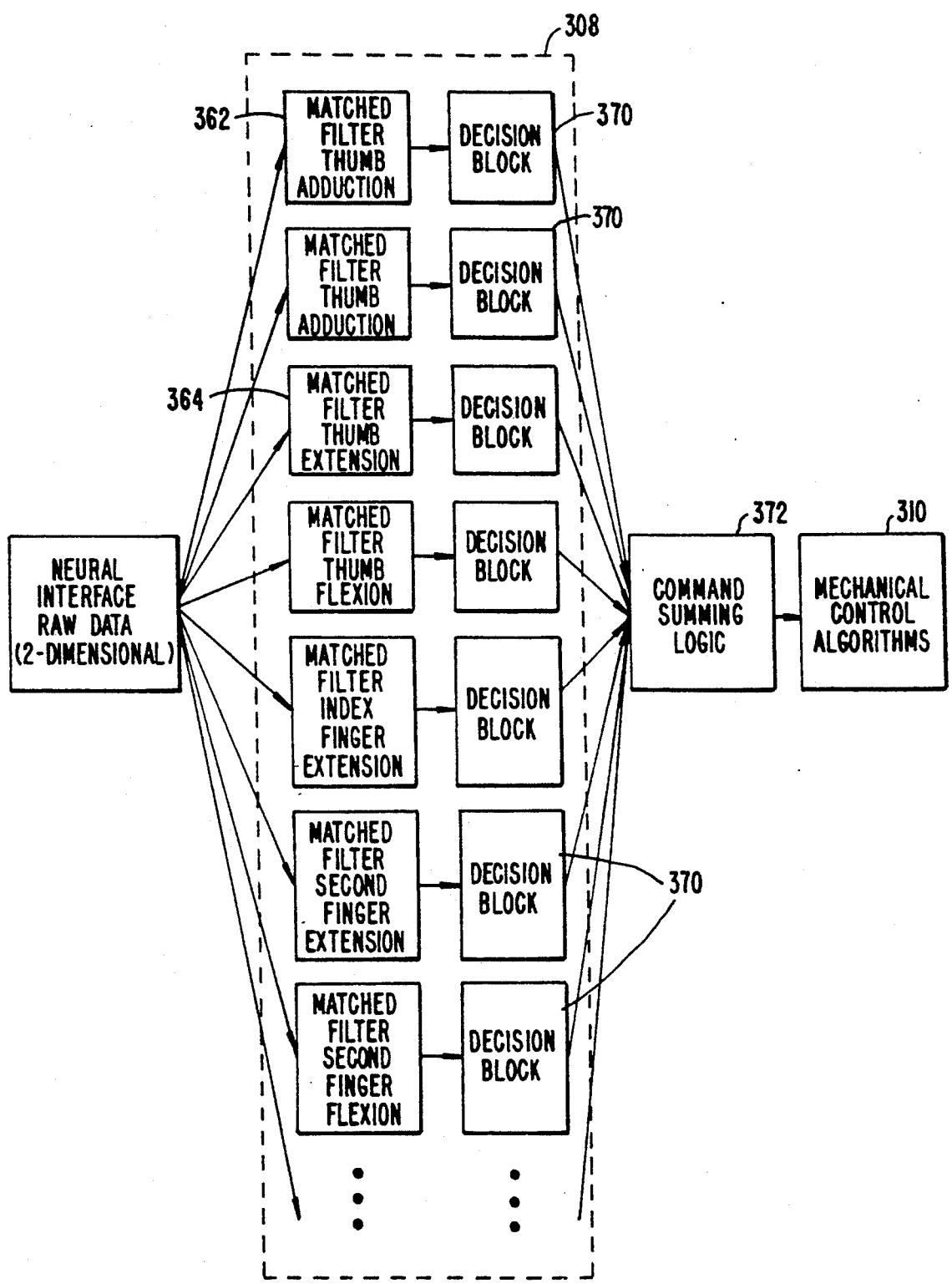
FIG. 11 is a block diagram illustrating the pattern matching algorithm of FIG. 10

FIG. 11 is a block diagram illustrating in more detail pattern matching block 308 of FIG. 10. As shown in FIG. 11, pattern matching block 308 contains a number of matched filters. Each matched filter stores a pattern of neural messages indicating a particular movement of the limb. Thus if the limb replaced by device 300 is a hand, matched filter 362 may store a pattern of neural messages indicating thumb adduction. Matched filter 364 may store a pattern of neural messages indicating thumb extension. When the two dimensional neural interface raw neural messages are received by block 308, such data are applied to each matched filter in the block for matching with the particular two dimensional pattern stored.

Each matched filter will compare the two dimensional data received with the pattern stored by a commonly known technique such as a correlation technique. Matched filters are well known in technology such as communications signal processing. For examples of matched filters, see:

1. Lathi, B. P., *Modern Digital and Analog Communication Systems*, CBS College Publishing, New York, N.Y., 1983, pp. 499–507;
2. Turin, G. L., *An Introduction to Matched Filters*, IRE Trans., Information Theory, Vol. IT-6, pp. 311–329, June, 1960;
3. Turin, G. L., *An Introduction to Digital Matched Filters*, Proc. IEEE, Vol. 64, pp. 1092–1112, July, 1976;
4. Stark, H. and Tuteur, F., *Modern Electrical Communications*, Prentice-Hall, Inc., Englewood Cliffs, N.J., 1979, pp. 478–515;
5. Couch, L. W., *Digital and Analog Communication Systems*, Macmillan Publishing Company, New York, N.Y., 1987, pp. 459–471.

In a nervous system, it is the number and frequency of the impulses, rather than their individual impulse characteristics, that determine the system behavior. For this reason, the two dimensional raw data received by block 308 resemble a two dimensional grid pattern of ones and zeros where the ones may represent the presence of action potentials at a particular location of the array 202 in the neural interface and a zero representing the absence of an action potential at such location. Such two dimensional pattern of ones and zeros is then matched with the pattern stored in each of the matched filters. Each matched filter will provide a signal indicating the extent of the matching detected by the filter.

The output of each filter is sampled, such as by closing a switch (not shown) between the filter and the decision block at the sampling instant, and applied to a decision block which may simply be a threshold detector which determines if the data pattern matching is strong enough to initiate the motion in question. The outputs from the decision blocks 370 are then summed by command summing logic 372 which synthesizes the overall command to the prosthesis and sends the results to control 310 which coordinates the operation of the appropriate mechanisms for moving structure 302. Thus if the neural information received by 308 matches both the patterns stored in filters 362, 364, the outputs of the two filters will be strong enough so that the decision blocks for such filters will provide outputs which are summed by logic 372. Control 310 will then cause the structure 302 to perform both the motions indicated by the patterns stored in filters 362, 364, namely thumb adduction and extension at the same time.

Sensors (not shown) may also be placed on the prosthetic limb 302 to for tactile, position and force sensing. Signals from such sensors are transmitted by transceiver 306 to transceiver 304 and through interface 200 or 250 to nerve 352 so that the person can realize tactile, position and force sensations. Such feedback will enhance the function of the prosthetic limb. The above described details in implementation and method are merely illustrative of the preferred embodiment of the invention. It is understood that the invention is to be limited only by the scope of the appended claims.

I claim:

1. A method for causing or detecting at least one action potential in a portion of a nervous system in a medium which contains ions by means of a device which comprises (a) a pair of microelectrodes supported on the same side of a carrier plate, and (b) means for applying or detecting an electrical potential deference between the pair when the portion of the nervous system is adjacent to the pair, said system and said medium being part of a human or animal body, said method comprising:

placing the pair of microelectrodes adjacent to each other and implanting said device into said body so that the pair of microelectrodes are adjacent to and alongside the portion of the nervous system and so that the portion is not between the microelectrodes; and applying a time-varying electrical potential across the microelectrodes so that the current caused by the potential across the microelectrodes is time-varying and passes from one microelectrode through the portion and then to the other microelectrode, so that the potential difference induced in the nervous system is localized to said portion.

2. The method of claim 1, wherein said pair of microelectrodes are substantially planar, and wherein said placing step places the two electrodes so that they are substantially in the same plane, said plane being adjacent to the portion of the nervous system.

3. The method of claim 1, wherein said applying step applies a time-varying electrical potential to one microelectrode of the pair of microelectrodes and a fixed D.C. electrical potential to the other microelectrode of the pair of microelectrodes.

4. The method of claim 1, wherein the pair of microelectrodes are located on one side of the carrier plate, said device further including a third electrode on the side of the plate opposite to said one side, wherein said applying step applies a time-varying electrical potential to both microelectrodes of the pair of microelectrodes and a fixed D.C. electrical potential to the third electrode.

5. The method of claim 1, wherein the pair of microelectrodes are located on one side of the carrier plate, said device further including a third electrode on the side of the plate opposite to said one side, wherein said applying step applies a time-varying electrical potential to one microelectrode of the pair of microelectrodes, a fixed D.C. electrical potential to other microelectrode and a fixed D.C. electrical potential to the third electrode.

6. The method of claim 1, wherein the pair of microelectrodes are located on one side of the carrier plate, said carrier plate having a hole therein between the pair of microelectrodes, said method further comprising placing an axon through said hole.

7. A device for causing or detecting change in electrical potential in a portion of a nervous system in a medium which contains ions, said system and said medium being part of a human or animal body, said device comprising:

a carrier plate;

a pair of microelectrodes on one side of said plate, said microelectrodes containing no ionic substance and each having a planar surface adapted to contact said medium; and means for applying or detecting a time-varying electrical potential difference between the planar surfaces of the pair when the portion of the nervous system is adjacent to the pair, wherein said pair of microelectrodes are located adjacent to each other so that when said electrical potential difference applying or detecting means applies a time-varying electrical potential difference between said pair when the portion of the nervous system is adjacent to the microelectrodes, the current passing between the pair is time-varying, between the planar surfaces of the microelectrodes, and substantially focused on the portion, so that a corresponding potential difference is induced in a localized portion of the nervous system.

8. The device of claim 7, further comprising:

another electrode on the side of said plate opposite to said one side, said another electrode having a planar surface adapted to contact said medium; and means for applying a reference potential to said another electrode, so that when said electrical potential difference is applied, current is passed between said planar surfaces of the microelectrodes and of said another electrode and so that said another electrode also provides electromagnetic shielding.

9. The device of claim 8, wherein said another electrode is connected to a reference potential.

10. The device of claim 7, wherein the portion is at least one axon and wherein said carrier plate has a hole between the pair of microelectrodes, wherein the planar microelectrodes are located side-by-side but do not substantially overlap and are separated from each other by the hole, and wherein the planar microelectrodes are shaped so that each of the two microelectrodes is larger in dimension at locations away from the hole than at locations adjacent to the hole, said hole having a shape adapted for passage of the axon(s).

11. The device of claim 7, wherein the pair of microelectrodes on one side of the plate are substantially coplanar so that both microelectrodes are adapted to be placed immediately adjacent to the portion for focusing current on the portion.

12. The device of claim 7, wherein said plate comprises a semiconducting material and the microelectrodes each comprises a metal layer over said carrier plate.

13. The device of claim 12, further comprising an insulating layer covering only a portion of each of the metal layers, leaving exposed only portions of the metal layers, so that when said applying step applies an electrical potential across the microelectrodes of the pair of microelectrodes, current will pass only between the exposed portions of the metal layers through the medium.

14. A device for measuring impedance in a portion of a nervous system in a medium which contains ions, said system and said medium being part of a human or animal body, said device comprising:

a pair of microelectrodes;

means for determining impedance between the pair, including means for passing a time-varying current between the pair through the movement of ions so that when the portion of the nervous system is adjacent to the pair, at least some of the current passes through said portion, and means for detecting the electrical potential between the pair; and means for connecting said current passing means and said detecting means to said pair.

15. The device of claim 14, wherein said detecting means includes a comparator or buffer amplifier and said connecting means connects said current passing means and said comparator or buffer amplifier to one of the microelectrodes through a common node.

16. A device for causing or detecting change in electrical potential in a medium containing ions, said device comprising:
   a pair of microelectrodes suitable for use in said medium wherein each of said microelectrodes has a planar surface and are located relative to each other so that the surfaces are located side-by-side but do not substantially overlap and are separated from each other by at least a region, and so that when electrical potential is applied between them and when the microelectrodes are placed in the medium, ion sin the medium will move between the planar surface of one microelectrode and the planar surface of the other microelectrode to cause an ionic current to flow through said region between the microelectrodes; and
   means for applying or detecting an electrical potential difference between the pair, wherein when said applying means applies an electrical potential difference between the pair said ionic current causes a change in electrical potential at said region, and wherein the planar surface of each of said pair of microelectrodes is shaped so that said surface is larger in dimension at locations away from the region than at locations adjacent to the region to focus the ionic current at or near the region, so that the effect of the ionic current is localized.

17. A device for causing or detecting change in electrical potential in nervous tissue located in a medium containing ions, said device comprising:
   a pair of microelectrodes adapted to be placed in said medium, wherein said microelectrodes each has a substantially planar surface, wherein said planar surfaces are located adjacent to each other and in a manner so that the surfaces are located side-by-side but do not substantially overlap each other, so that when electrical potential is applied between them, ions in the medium will move between the planar surfaces of the pair of microelectrode plates causing ionic current to pass between the microelectrodes; and
   means for applying or detecting an electrical potential difference between the pair, wherein the planar surface of each of said pair of microelectrodes is shaped so that each of the two planar surfaces is larger in dimension at locations away from the other planar surface than at locations adjacent to the other planar surface to focus the ionic current on locations between or adjacent to the two surfaces, so that when nervous tissue is placed in between or adjacent to the surfaces, an action potential is induced in a localized portion of the nervous tissue.

18. The device of claim 17, wherein said pair of microelectrodes are plates.

19. The device of claim 17, wherein each of said pair of microelectrodes comprises a semiconducting substrate and a layer of electrically conductive material over said substrate, and wherein a portion of a surface of the layer forms said planar surface of the microelectrode.

20. The device of claim 19, wherein each of said microelectrodes further comprises a layer of electrically insulating material covering predetermined portions of the layer of electrically conductive material, so that a surface of the uncovered portion of the electrically conductive material layer is adapted to contact the medium and defines the planar surface.

21. The device of claim 17, wherein said two planar surfaces are substantially coplanar.

22. The device of claim 17, said device further comprising insulator means for insulating portions of the microelectrodes leaving only predetermined portions of the microelectrodes exposed, so that the planar surface of each microelectrode is defined by the exposed portion or portions of the microelectrode.

23. The device of claim 17, wherein the planar surface of each microelectrode is substantially semicircular or parabolic in shape.

24. The device of claim 17, further comprising a carrier plate having an aperture therein suitable for passage of one or more axons, wherein each microelectrode comprises a layer of electrically conductive material supported by the carrier plate, the layer of each microelectrode separated from the other microelectrode layer by the aperture.

* * * * *

UNITED STATES PATENT AND TRADEMARK OFFICE
CERTIFICATE OF CORRECTION

PATENT NO.   :   5,178,161
DATED        :   January 12, 1993
INVENTOR(S)  :   Gregory T. A. Kovacs It is certified that error appears in the above-identified patent and that said Letters Patent is hereby corrected as shown below:

Column 15, Lines 10-11, in Claim 1:   Replace "deference" with --difference--

Column 17, Line 20, in Claim 16:   Replace "ion sin" with --ions in--

Signed and Sealed this

Seventh Day of June, 1994

Attest:

BRUCE LEHMAN

Attesting Officer    Commissioner of Patents and Trademarks